United States Patent [19]

Nowacki et al.

[11] Patent Number: 4,538,620

[45] Date of Patent: Sep. 3, 1985

[54] INHALATION VALVE

[75] Inventors: Christopher Nowacki, Arlington Heights; Alfred G. Brisson, Schaumburg, both of Ill.

[73] Assignee: Trutek Research Inc., Arlington Hts., Ill.

[21] Appl. No.: 494,256

[22] Filed: May 13, 1983

[51] Int. Cl.³ .............................................. A61B 5/08
[52] U.S. Cl. .............................. 128/725; 128/205.23; 128/207.16; 137/102
[58] Field of Search .......... 128/725, 720, 728, 203.11, 128/205.24, 203.28, 205.12, 205.13, 205.14, 205.17, 206.15, 207.12, 207.14, 207.16, 202.26, 205.23; 137/512.4, 512.15, 493.8, 102

[56] References Cited

U.S. PATENT DOCUMENTS 3,165,067 1/1965 Greenwald ...................... 137/512.4
4,259,951 4/1981 Chernack et al. ............... 128/205.24
4,437,490 3/1984 Demers et al. .................. 137/512.4

Primary Examiner—Henry J. Recla
Attorney, Agent, or Firm—Trexler, Bushnell & Wolters, Ltd.

[57] ABSTRACT

An inhalation valve for respiratory diagnosis and/or therapy is provided. A single rubber or the like diaphragm is mounted in a free floating fashion so that one portion would open upon inhalation, while the other portion opens upon exhalation. The valve body is of molded plastic construction and contains a tube of restricted area through which air flows upon inhalation with reduction in lateral pressure being measured to indicate the volume of inhaled air.

4 Claims, 5 Drawing Figures

INHALATION VALVE

BACKGROUND OF THE INVENTION

In the treatment of patients suffering from various respiratory problems, either of acute or chronic nature, involving the lungs, bronchia, etc., it is often necessary to test the breathing capacity of the patient. Prior art devices or apparatus for this purpose have tended to either be quite expensive or of a low degree of accuracy. An improved inhalation valve for such purposes, and which has attained a substantial degree of commercial acceptance, is disclosed in our prior application Ser. No. 394,403, filed July 1, 1982 for "Inhalation Valve". In our prior inhalation valve, a restricted inlet passage was provided in which a reduced pressure was developed upon inhalation. This inlet passage was displaced to one side of the main passage to which it was joined by a tortuous flow path. A single diaphragm or flapper valve closed off the main passage upon inhalation and allowed it to open upon exhalation.

OBJECTS AND SUMMARY OF THE PRESENT INVENTION

It is an object of the present invention to provide an inhalation valve having a portion to be placed in a patient's mouth while the patient inhales and exhales. The valve is of improved and simplified construction.

A further object of the present invention is to provide such an inhalation valve having a single diaphragm or flapper valve having two active portions, respectively opened and closed upon inhalation and exhalation.

In attaining the foregoing objects of the present invention we provide an inhalation valve having a plastic molded housing having a large flow path therethrough and having a relatively small diameter tube in the flow path which causes a drop in lateral pressure upon inhalation therethrough. A single rubber or the like diaphragm is supported across the flow path with suitable backing on one face thereof in the upper portion of the diaphragm with backing on the opposite face in the lower portion of the diaphragm so that the upper portion of the diaphragm will deflect upon exhalation, while the lower portion thereof will deflect upon inhalation, thus controlling air flow through the inhalation valve.

THE DRAWINGS

The present invention will best be understood with reference to the following specification taken in connection with the accompanying drawings wherein.

DETAILED DESCRIPTION OF THE ILLUSTRATIVE EMBODIMENT

Figure 1:
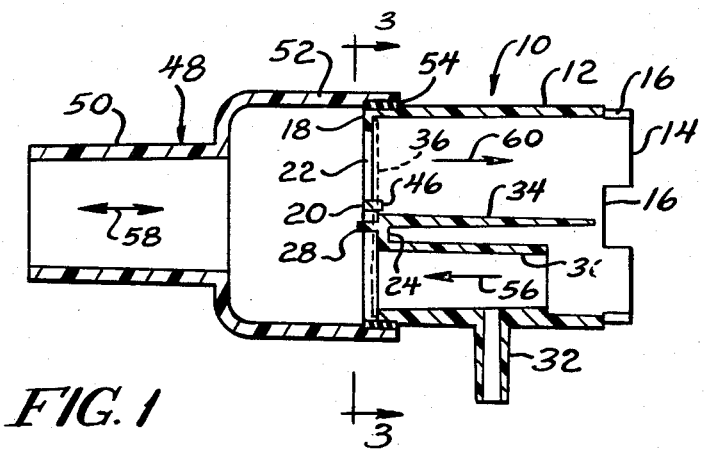
FIG. 1 is an axial sectional view through the inhalation valve forming the subject matter of the present invention.

Turning now in greater particularity to the drawings, there will be seen an inhalation valve 10 constructed in accordance with the principles of the present invention.

The valve includes a cylindrical body 12 of molded plastic construction having an open end 14 with a plurality of arcuately spaced notches 16 therein. There are four notches shown as exemplary, and the total area of these four notches is greater than the cross section of an inhalation tube to be described shortly hereinafter. This provides an anti-cheat feature preventing a patient from placing his hand across the end 14 of the body while inhaling to produce a pressure drop, thereby to produce an apparently greater inhalation than actually is made.

At the opposite end of the body 12 in the upper portion thereof there is a wall portion including an upper arcuate section 18 of nearly a semi-circle in extent having the ends thereof connected by a transverse rib 20 which is spaced just above a diameter of the body 12. This provides an opening 22 which is essentially a segment of a circle.

A transverse wall 24 is spaced down from the rib 20 very slightly, leaving a diametral gap 26. This wall or plate 24 also is displaced to the right (FIG. 1) of the arc 18 and rib 20 by a slight distance. A rectangular tongue 28 extends to the left (FIG. 1) from the wall 24 and is of restricted dimension relative to the diameter of the body 12, being centrally disposed and on the order of ⅛ the diameter. The purpose for this tongue will be set forth hereinafter.

An inhalation tube 30 of reduced diameter opens through the wall 24 and lies tangent to the wall of the body 12 along the bottom portion thereof, extending from the wall 24 approximately ¾ of the distance toward the end 14. The tube 30 tapers somewhat in diameter, being slightly larger at the left end than at the right end. Relatively toward the right end of the tube 30 there is provided a transverse fitting 32 for a flexible tube of plastic or rubber. The fitting 32 is hollow and communicates with the interior of the tube 30.

A horizontal partition 34 extends from the right side of the wall 24 nearly to the end 14, terminating somewhat short thereof, and tapering from a maximum thickness at the wall to a minimum thickness at the far end.

Figure 2:
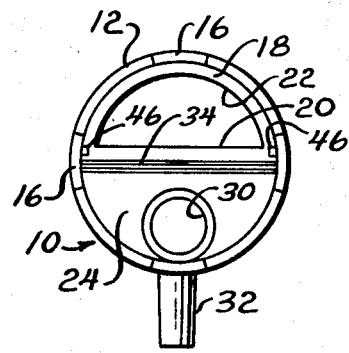
FIG. 2 is an end view of the inhalation valve taken from the right end in FIG. 1.
Figure 3:
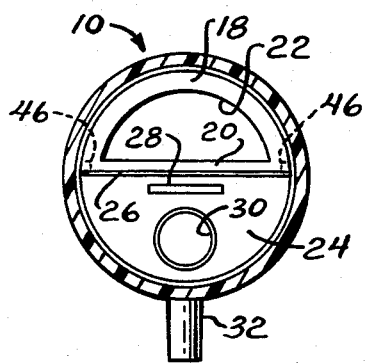
FIG. 3 is a cross sectional view through the valve taken substantially along the line 3—3 in FIG. 1.
Figure 4:
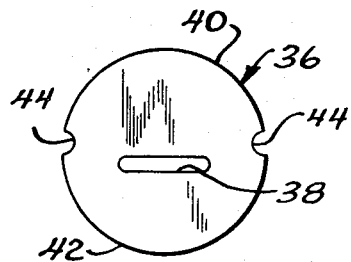
FIG. 4 is a plan view of the diaphragm of the valve.
Figure 5:
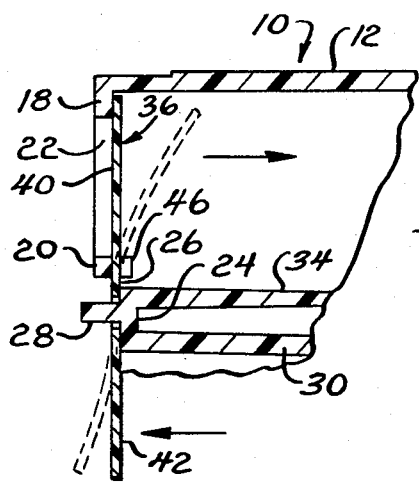
FIG. 5 is an enlarged detail view similar to a portion of FIG. 1 and showing operation of the diaphragm.

The inhalation valve further includes a diaphragm 36 shown in broken lines in FIG. 1 and in full lines in FIG. 5, and omitted from FIGS. 2 and 3 for clarity of illustration. The diaphragm is made of a flexible material such as synthetic rubber or plastic, or of other such material, and as best seen in FIG. 4 is substantially circular in shape. Slightly below the median line it is provided with a slot 38 for receipt of the tongue 28 for mounting of the diaphragm. The upper portion 40 of the diaphragm lies inwardly of the arcuate section 18 and rib 20, fitting against the back side thereof as best seen in FIG. 5 in solid lines. The lower portion 42 lies against the front of the wall 24 with the central portion of the diaphragm extending through the slot 26. Opposite notches 44 which lie nearly diametrically relative to one another are provided in the diaphragm, and these interfit with protuberances 46 on the wall of the body 12 and the rib 20 which coact with the tongue 28 to hold the diaphragm in proper position. It is important to note that the diaphragm is free floating. If it were clamped in any way the diaphragm could crimp or otherwise inhibit flexing, thus offering greater resistance to opening and providing a false signal.

A mouthpiece 48 is provided having a tubular portion 50 adapted to fit into a patient's mouth, and an enlarged portion 52 adapted for assembly with the body 12. A gasket 54 of rubber or the like lies between the mouthpiece and the body 12 to insure an airtight seal.

When a patient inserts the tubular portion 50 of the mouthpiece in his mouth and inhales, the lower portion 42 of the gasket will deflect to the left as shown in broken lines in FIG. 5, thereby permitting air to flow through the tube 30 as indicated by the arrow 56 in FIG. 1. The top portion 40 of the diaphragm lies against the arcuate member 18 of the rib 20 to prevent air flow through the upper portion of the body 12 and through the aperture 22. Air flow through the restricted tube 30 causes a drop in lateral pressure which is transmitted through the fittings 32 and a plastic or rubber hose to a transducer such as that disclosed in our co-pending application Ser. No. 415,735 filed Sept. 7, 1982 for Inhalation Transducer Circuit, and assigned to the same assignee as the present invention, namely Trutek Research, Inc., 3436 North Kennicott, Arlington Heights, Ill., 60004. Air flow continues through the mouthpiece to the left as indicated by the double ended arrow 58 in FIG. 1. Conversely, on exhalation the lower gasket portion 42 presses tight against the wall 24 and seals off the tube 30. However, the upper portion 40 of the gasket deflects to the right as shown in broken lines in FIG. 5, so that air passes to the right as indicated by the arrow 60 in the upper portion of the body 12, such exhaled air simply being dispelled into the atmosphere.

The body and diaphragm assembly may be used repeatedly if so desired, with only the mouthpiece being replaced for a new patient. The mouthpiece itself may be used indefinitely by the same patient. However, since the entire assembly is made of molded plastic and an inexpensive piece of sheet rubber or the like, the entire inhalation valve assembly may be discarded after use by a given patient, and it is expected that this would be done if the patient suffered from a respiratory infection.

The wall or shelf 34 isolates the tube 30 from the exhalation flow path indicated by the arrow 60, and therefore prevents the development of any false signal.

The inhalation valve as now completely shown and described is remarkably simple and is easy to mold of a suitable plastic material. The cost is quite low. The single diaphragm which operates in both directions with different halves thereof is inexpensive, while the necessity of mounting only a single diaphragm reduces assembly costs. Accordingly, an inexpensive and simple inhalation valve is provided. The two-way valve is functionally superior to a one-way valve that must be removed from the patient's mouth for exhalation. As will be apparent, the reduction in lateral pressure of air flow through the tube 50 as indicated by the arrow 56 is compared with ambient pressure to produce the desired readout in the accompanying electronic circuitry.

The specific example of the invention as herein shown and described is for illustrative purposes. Various changes in the structure will no doubt occur to those skilled in the art and will be understood as forming a part of the present invention insofar as they fall within the spirit and scope of the appended claims.

The invention is claimed as follows:

1. An inhalation valve comprising a cylindrical body of predetermined diameter to provide bidirectional flow therethrough and having an open first end and an open second end, a cylindrical mouthpiece joined to said body at said second end and forming a straight-through continuation of said body, a flow tube substantially smaller diameter than said predetermined diameter disposed within said body adjacent to and connected to one side thereof and oriented axially thereof and open at both ends providing an inhalation flow path through said body, partition means disposed substantially diametrically of said body and extending substantially from said first end substantially to said second end and demarcating a portion of said body exteriorly of said tube as an exhalation flow path, a single substantially circular flexible diaphragm, means mounting said diaphragm substantially diametrically thereof at the second end of said body with first and second portions of said diaphragm respectively lying across said inhalation and said exhalation flow paths, a transverse wall covering substantially half of said second end of said body and through which said flow tube opens, said wall being upstream of said diaphragm and forming a back-up for the second portion of said diaphragm to prevent exhalation through said flow tube and permitting flexing of said second portion of the diaphragm to permit inhalation through said flow tube, back-up means downstream of said diaphragm for the first portion of said diaphragm permitting flexing of said diaphragm first portion upon exhalation and backing up said diaphragm first portion upon inhalation to permit exhalation but prevent inhalation through said exhalation flow path, and means extending laterally through said flow tube and said body providing a lateral opening from said flow tube to permit detecting a lateral pressure drop upon inhalation.

2. An inhalation valve as set forth in claim 1 wherein said diaphragm has an aperture substantially on a diameter thereof, and wherein said mounting means includes locater means on and extending axially from said partition and through said aperture, said diaphragm being otherwise substantially imperforate.

3. An inhalation valve as set forth in claim 1 wherein said partition means includes a substantially diametral wall extending from near the entering end of said body to said transverse wall.

4. An inhalation valve as set forth in claim 1 wherein said cylindrical body has a plurality of edge-opening arcuately spaced recesses extending axially thereinto at the first end to prevent blocking of air flow through said body such as by the palm of a hand.

* * * * *